US 8,382,408 B2

(12) United States Patent
Sun et al.

(10) Patent No.: US 8,382,408 B2
(45) Date of Patent: Feb. 26, 2013

(54) TRAILER SYSTEM FOR INSPECTING VEHICLES AND INSPECTION SYSTEM HAVING THE SAME

(75) Inventors: Shangmin Sun, Beijing (CN); Zhongrong Yang, Beijing (CN); Nan Jiang, Beijing (CN); Guang Yang, Beijing (CN)

(73) Assignee: Nuctech Company Limited, Beijing (CN)

( * ) Notice: Subject to any disclaimer, the term of this patent is extended or adjusted under 35 U.S.C. 154(b) by 203 days.

(21) Appl. No.: 11/992,767

(22) PCT Filed: Oct. 11, 2007

(86) PCT No.: PCT/CN2007/002924
§ 371 (c)(1),
(2), (4) Date: Mar. 28, 2008

(87) PCT Pub. No.: WO2008/052412
PCT Pub. Date: May 8, 2008

(65) Prior Publication Data
US 2010/0028099 A1 Feb. 4, 2010

(51) Int. Cl.
*B60P 3/06* (2006.01)
(52) U.S. Cl. ..................................... 410/67
(58) Field of Classification Search .............. 410/7, 19, 410/30, 45, 56, 57, 65, 67; 414/222.01, 571; 105/355, 362
See application file for complete search history.

(56) References Cited

U.S. PATENT DOCUMENTS

| 4,804,302 | A | * | 2/1989 | Andre ............................ 410/19 |
| 4,929,133 | A | * | 5/1990 | Wiseman ........................ 410/52 |
| 4,942,828 | A | * | 7/1990 | Walz et al. .................... 108/55.5 |
| 6,542,580 | B1 | | 4/2003 | Carver et al. |
| 6,837,657 | B2 | | 1/2005 | Li et al. |
| 7,059,814 | B2 | | 6/2006 | Su et al. |
| 7,367,764 | B2 | * | 5/2008 | Li et al. ............................ 410/65 |
| 2004/0265083 | A1 | | 12/2004 | Johnson |
| 2005/0084357 | A1 | | 4/2005 | Su et al. |

FOREIGN PATENT DOCUMENTS

| CN | 1324751 A | 12/2001 |
| CN | 1126705 | 11/2003 |
| CN | 1500685 A | 6/2004 |
| CN | 1607122 A | 4/2005 |
| CN | 1607135 A | 4/2005 |
| CN | 1309609 | 4/2007 |
| DE | 103 53 484 A1 | 6/2004 |
| DE | 10 2004 050 661 B3 | 6/2005 |
| KR | 598654 | 7/2006 |

* cited by examiner

*Primary Examiner* — H Gutman
(74) *Attorney, Agent, or Firm* — Jacobson Holman PLLC

(57) ABSTRACT

A trailer system for inspecting a vehicle inspection includes a trailer having a trailer body, the trailer bearing a vehicle to be inspected, a turning member rotatably provided on an upper surface of the trailer for abutting against wheels of the vehicle to be inspected that has halted on the trailer, and a turning plate rotation driving mechanism provided on the trailer for driving the turning plate to turn toward the upper surface of the trailer. The trailer system can trail the trailer with various loads passing through an inspection system such as a scanning passage, while bearing a heavy load, and maintaining the strength and rigidity thereof without damaging the vehicle to be inspected. A radiation imaging inspection system includes the trailer system.

9 Claims, 4 Drawing Sheets

TRAILER SYSTEM FOR INSPECTING VEHICLES AND INSPECTION SYSTEM HAVING THE SAME

CROSS-REFERENCE TO RELATED APPLICATION

This is a national stage of PCT/CN07/002924 filed Oct. 11, 2007 and published in Chinese.

BACKGROUND OF THE INVENTION

1. Field of the Invention

The present invention relates to a trailing device in trailing art, more especially, to a trailer system for inspecting a vehicle and an inspection system having the same which are widely used in radiation imaging inspection.

2. Description of the Related Art

Trailers are always used in radiation imaging inspection.

The radiation imaging inspection is indispensable for customs, civil airport and railway station. A system used in radiation imaging inspection is normally operated as follows: a radiation source and detector arrays capable of receiving detecting rays penetrating through a vehicle to be inspected are provided in a detecting passage that can shield rays; the vehicle to be inspected is trailed through radiating beams for inspection by a special trailing device. And the system generally comprises subsystems such as an accelerator, a detector, a image acquiring and scanning device, and a running and inspecting device. During inspection, the vehicle to be inspected rapidly passes through the scanning passage, which is essential to the radiation imaging inspection. In prior art, the special trailing device includes a flat car and various trailing bogies or the like.

Chinese Patent No. CN00107480.6 discloses an automatic flatcar for a fixed container inspection system. During inspection, the vehicle to be inspected is driven onto the automatic flatcar. Longitudinal and horizontal travel mechanisms are installed at the bottom of the automatic flatcar, and the travel mechanisms circulate or reciprocate on rectangular rails so that the vehicle to be inspected is smoothly transmitted through the scanning passage. However, the automatic flatcar has following disadvantages: it has to bear total weight of the vehicle to be inspected including the cargo. In addition, the automatic flatcar has a large trailer body with complex structure, which leads to high cost and maintenance fees.

On the other hand, Chinese Patent No. CN200310100184.0discloses a trailer for a radiation imaging trailer system. The trailer comprises a trailer frame, vehicle wheels and turning member. During working, the trailer only drags front wheels of the vehicle to be inspected, and the rear wheels 203 follow accordingly. There is a climbing slope and a declining slope at both ends of the trailer frame, and a turning member on the trailer frame. During inspection, the turning plate abuts against the front wheels of the vehicle to be inspected, and the vehicle to be inspected is dragged through the scanning passage by the trailer. According to the solution disclosed therein, when the vehicle to be inspected runs away from the trailer, since, on one hand, the turning plate is opened, it may scrape the chassis, oil tank and other components, at the bottom of the vehicle to be inspected. On the other hand, since the climbing and declining slopes are provided on the trailer, the length of the trailer is not enough for structural restraints, for the vehicle to be inspected having longer wheelbase, the front wheels has left the trailers where as the rear wheels 203 thereof has not left the trailers yet during unloading of the vehicle to be inspected, which may cause the vehicle to straddle over the trailer. In addition, this may also leads to the chassis to be inspected and the bottom attachments being scraped by the trailer easily, thus the vehicle to be inspected is damaged, which may further influence the normal working of the radiation imaging system. Therefore, the invention thereof reduces the reliability of the system when used for the radiation imaging system. Especially, the invention is not adapted for trailing heavily loaded vehicle with low chassis and long wheelbase.

SUMMARY OF INVENTION

In view of the above disadvantages in the conventional art, it is an object of the present invention to provide a trailer system for inspection system trailing vehicle to be inspected with various loads safely through a scanning passage. The trailer system can bear heavy load while maintaining strength and rigidty thereof.

Another object of the invention is to provide a radiation imaging inspection system using the trailer system for inspecting a vehicle, the inspection system thereof can harmlessly undertake radiation imaging inspection for the vehicle to be inspected using said trailer system.

Additional aspects and/or advantages of the invention will be thoroughly understood with reference to the description hereafter in combination with accompanying figures, or learned by practice of the invention.

The object of the invention is achieved by providing a trailer system for inspecting a vehicle, comprising:

a trailer having a trailer body, the trailer bearing a vehicle to be inspected;

a turning member, such as a turning plate, rotatably provided on an upper surface of the trailer for abutting against wheels of the vehicle to be inspected halting on the trailer; and a turning member rotation driving mechanism provided on the trailer for driving the turning member to be rotatable.

According to an aspect of the invention, the trailer body has a trailer frame.

According to an aspect of the invention, the trailer system further comprises a floor auxiliary device provided opposing to the trailer in a running direction of the vehicle to be inspected.

According to an aspect of the invention, the turning member rotation driving mechanism, configured as a turning plate rotation driving mechanism 25 comprises a linkage 29 with an end 30 thereof connected to the turning plate 12; and an actuating device with an end thereof attached to the other 31 of the linkage device to the drive the linkage device when the actuating device is applied with an external force so that the turning member is rotated.

According to an aspect of the invention, the linkage device comprises a chain connected to the turning member.

According to an aspect of the invention, the actuating device comprises: a guiding rod, with an end thereof connected to the chain; a spring fitting over the guiding rod at a side near the floor auxiliary device, and elastic force from the spring straining the guiding rod before the guiding rod is pressed; and a bumping shaft coupled with the guiding rod so that the force applied on the guiding rod is counteracted when the bumping shaft is applied with the external force, which leads to the turning member rotating toward the upper surface of the trailer.

According to an aspect of the invention, the floor auxiliary device comprises a bumping block provided at a position on the floor auxiliary device which is opposed to the guiding rod.

According to an aspect of the invention, the turning plate rotation driving mechanism comprises a turning plate brake position adjusting device for adjusting height and angle of the turning plate abutting against the front wheels halting on the trailer.

According to an aspect of the invention, the turning member brake position adjusting device is an adjusting sleeve fitted over the guiding rod, with an end thereof abutting against the spring to adjust the brake height and angle of the turning member by the adjustment of the tension degree of the spring.

According to an aspect of the invention, the trailer frame comprises a positioning recess provided in a running direction of the vehicle to be inspected facing away from the turning member, to be coupled with the turning member for positioning the front wheels of the vehicle to be inspected.

According to an aspect of the invention, the turning member comprises a turning plate pivotably attached to the trailer body.

According to an aspect of the invention, the height at both ends of the trailer frame is higher than that at the middle portion to form a concave structure, so that the vehicle to be inspected is not scraped by the middle portion.

Thus, when the vehicle to be inspected is trailed by the trailer for inspection, the lower middle portion is the main bearing portion of the trailer.

According to an aspect of the invention, the floor auxiliary device comprises a declining slope device provided at a side toward exit direction of the trailer by a certain distance.

According to an aspect of the invention, the trailer body further comprises wheel set units provided at both sides of the trailer frame.

According to an aspect of the invention, the trailer body has four wheel set units.

According to an aspect of the invention, each wheel set unit comprises: a structural member to be engaged to the trailer frame; and the wheel is provided on the structural member. Thus, according to the above description, the wheel set unit can be separately assembled, then the wheel set unit is integrally formed with the trailer frame, the other units can be positioned integrally by the mechanical machining surface on the trailer frame. And a structure with separate units whereas integrally positioned is achieved, which further reduces the height of the trailer body and easiness of disassembly and maintenance.

According to an aspect of the invention, there is wheel flange formed at the inner side of the wheel in the wheel set unit for guiding during the running of the trailer.

According to an aspect of the invention, the wheel set unit can be independently installed. Thus, the strength and rigidity of the trailer is ensured and the assembly is convenient.

According to an aspect of the invention, the floor auxiliary device further comprises an auxiliary supporting member provided at lower part of the trailer frame corresponding to the abutting position of the trailer, when the rear axis of the vehicle to be inspected passes by the trailer, the height of the auxiliary supporting member can provide support when the trailer frame deforms.

According to an aspect of the invention, the supporting height of the auxiliary supporting member is adjustable.

According to another aspect of the invention, a radiation imaging inspection system is provided, comprising an accelerator, a detector, an image acquisition device, a scanning device, an operation and inspection subsystem, and a trailer system for inspecting a vehicle according to an aspect of the invention, the trailer system comprising: a trailer having a trailer body, the trailer bearing a vehicle to be inspected; a turning member, such as a turning plate, rotatably provided on an upper surface of the trailer, for abutting against wheels of the vehicle to be inspected halting on the trailer; and a turning member rotation driving mechanism provided on the trailer for driving the turning member to turn toward the upper surface of the trailer.

Meanwhile, according to above solution, additional features as follows can be provided: since the declining slope fixed at the exit position has a certain length, a vehicle straddling over the trailer can be avoided otherwise the bottom chassis may be damaged accordingly.

Compared with conventional art, it can be found that the present invention has a simple design and configuration, which not only reduces the height of the trailer but also ensures the strength and rigidity of the trailer, and thus the vehicle to be inspected can pass special detecting facilities, such as a scanning passage, safely without being scraped or damaging the chassis of the vehicle to be inspected and the attachments thereof.

BRIEF DESCRIPTION OF THE DRAWINGS

Further disclosure, objects, advantages and aspects of the present invention may be better understood by those skilled in the relevant art by reference to the following description of embodiments taken in conjunction with the accompanying drawings, which are given by way of illustration only, and thus are not limitative of the present invention, and in which.

DETAILED DESCRIPTION OF THE PREFERRED EMBODIMENTS

Figure 1:
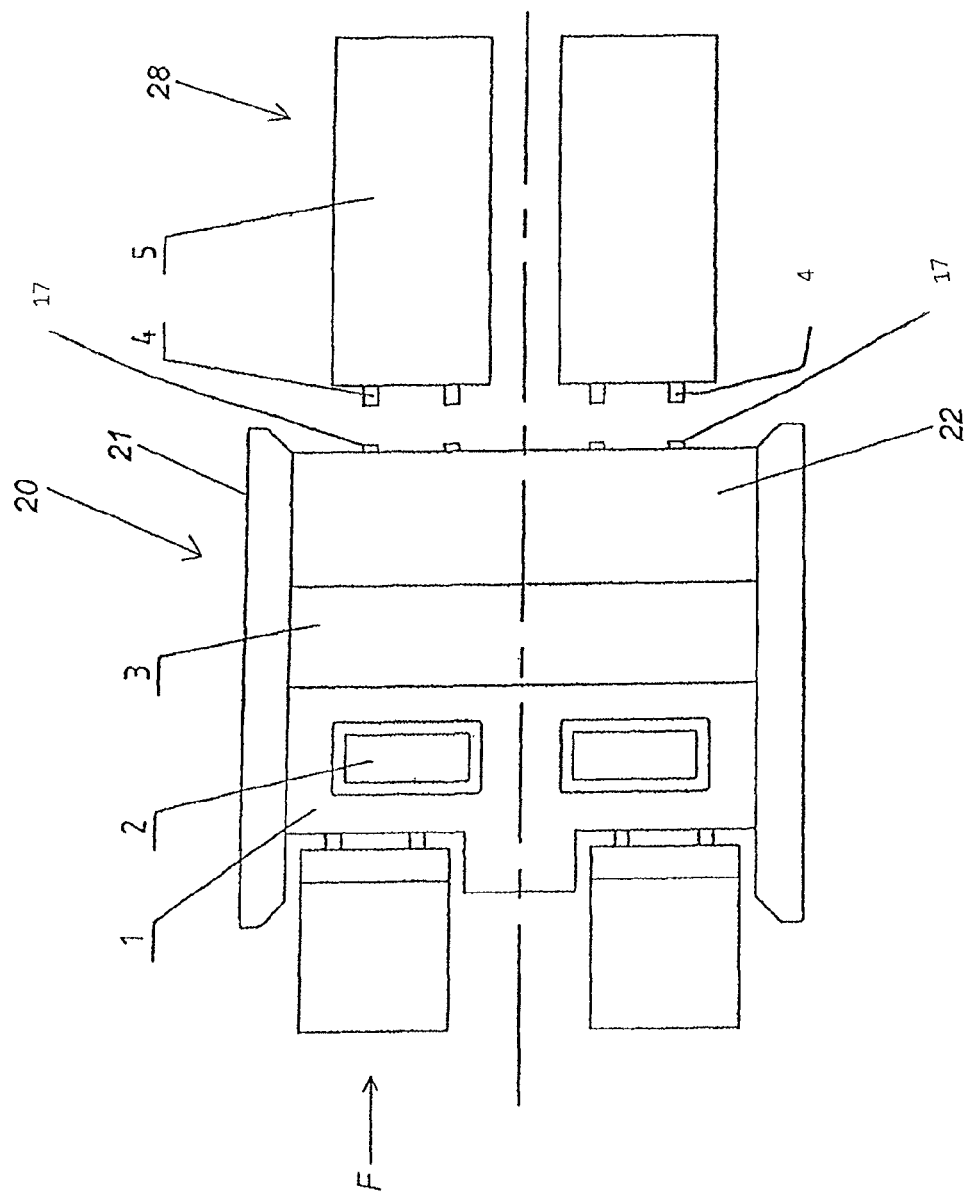
FIG. 1 shows a plan view of a trailer system for inspecting a vehicle according to an embodiment of the invention.

Above and other aspects of features of the present invention will be become readily apparent with preferred embodiment and referenced to accompany drawing by a detail description hereinafter, wherein the same reference numerals refer to the same elements throughout the specification.

Meanwhile, in the following embodiment, although a case in which the trailer system for inspecting a vehicle is used in vehicle radiation imaging inspection is described in detail, it is appreciated for a person skilled in the art that the present invention can be applied to other related vehicle inspection without deviating from the scope and the spirit of the present invention.

With reference to FIG. 1 showing a plan view of a trailer system for inspecting a vehicle 24 according to an embodiment of the invention, the trailer system thereof comprises a trailer body 21 and a floor auxiliary device 26. The trailer 20 bears the vehicle to be inspected for different inspection purposes, and the floor auxiliary device 26 prevents a bottom of the vehicle 24 that is being inspected from contacting the trailer 20 in a manner that might damage the bottom of the vehicle, thus overcoming a shortcoming associated with prior art devices.

Figure 4:
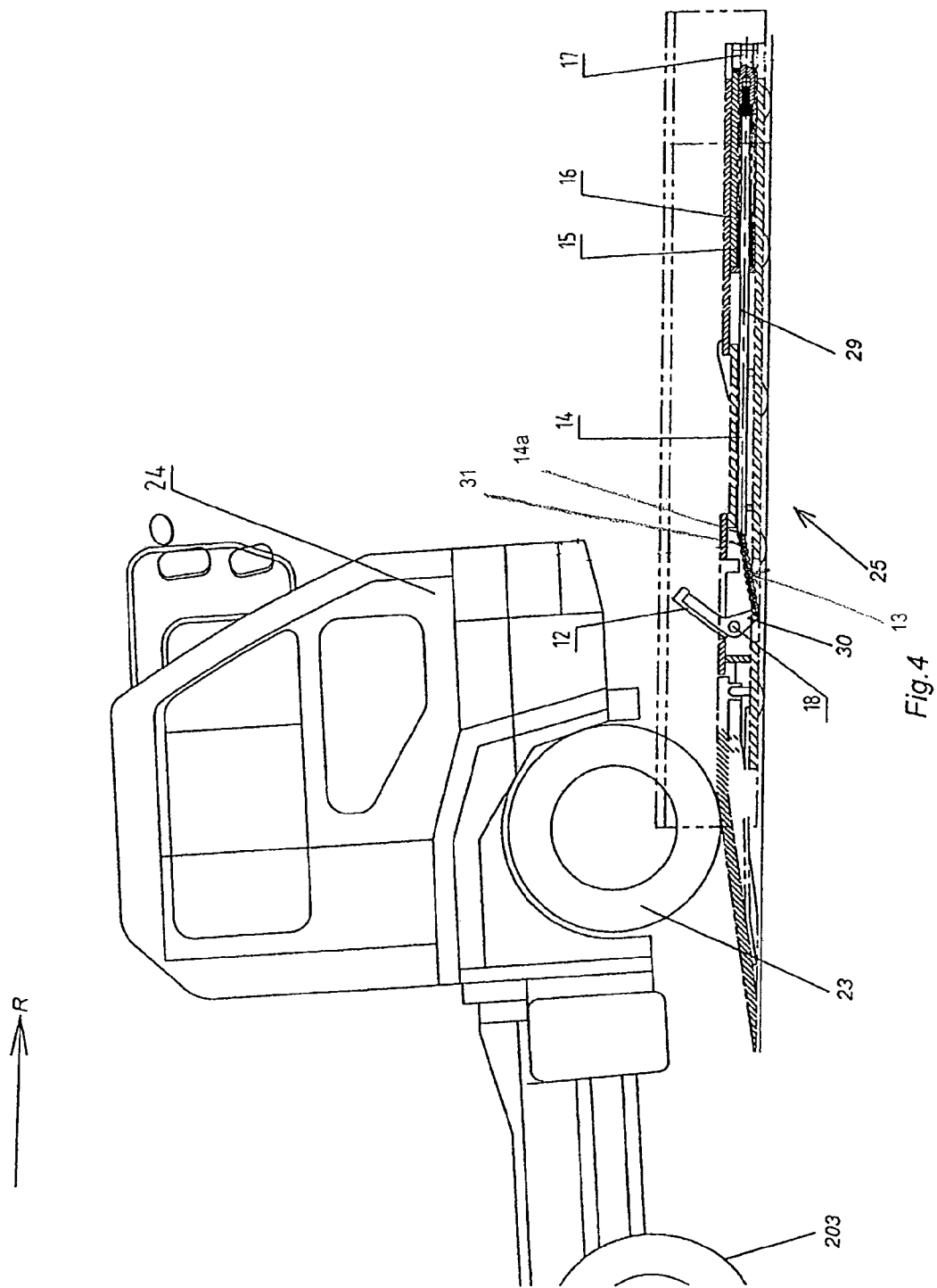
FIG. 4 shows a schematic view of a turning member of a trailer in the trailer system for inspecting the vehicle according to an embodiment of the invention.

The trailer body comprises a trailer frame 1, a turning member 2, a positioning recess 3 and a wheel set unit 7 (not shown in FIG. 1). The detailed structures of the turning member 2 and wheel set unit 7 will be described in detail in the following description. The turning member 2 in the present invention is implemented in the form of a plate, i.e., the turning plate 12 as depicted in FIG. 4. However, it is evident to a person skilled in the art that it is possible to substitute for the turning plate 2 by 12 a halting plate, a rotatable positioning plate or a rotatable rail or the like.

Figure 2:
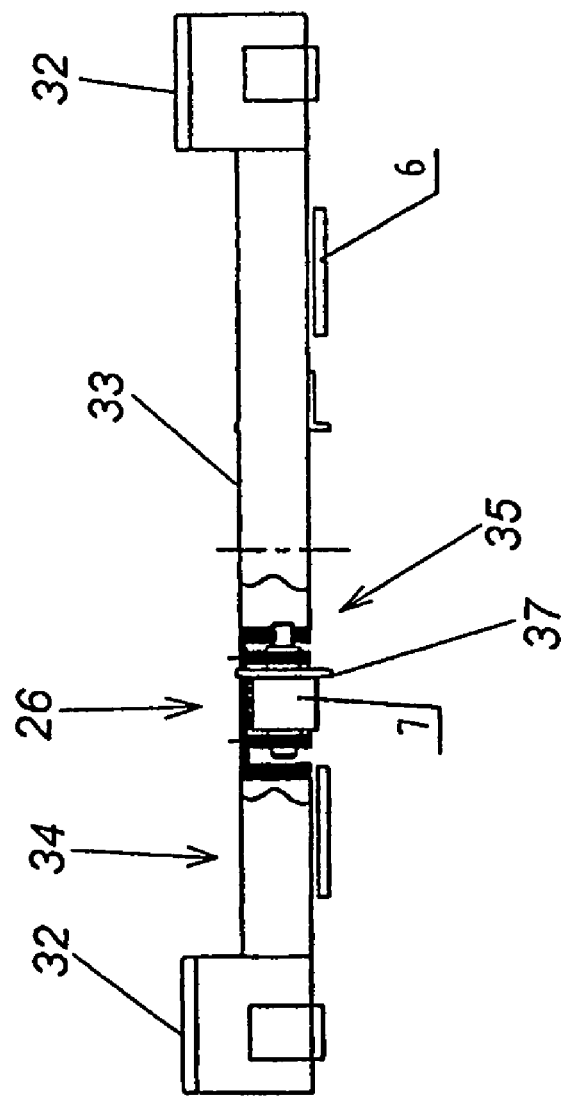
FIG. 2 shows an end view of a trailer system for inspecting the vehicle according to an embodiment of the invention.

The floor auxiliary device 26 comprises a declining slope 5, an auxiliary supporting member 6 (as shown in FIG. 2), the detailed structure of the auxiliary supporting member 6 will be described in the following description. A bumping block 4 is provided at a side of the declining slope 5 toward the trailer.

The declining slope 5 is fixed at an exit position, i.e., the declining slope 5 is provided at a side of the trailer toward the exit position by a certain distance. Of course, the distance can be appropriately adjusted as required by circumstances. Since the declining slope has a certain length, any scraping of the bottom of the vehicle due to the vehicle straddling over the trailer is avoided.

The height at both ends 32, 32 of the trailer frame 1 is higher than that at the middle portion 33 to form a concave structure 34, so that the vehicle to be inspected is not scraped by the middle portion 33. Meanwhile, the trailer frame 1 supports the vehicle to be inspected on its upper surface 22.

The wheel set unit 7, the auxiliary supporting member 6 in the trailer system for vehicle inspection according to an embodiment of the invention will be further described in detail with reference to FIGS. 2-3.

FIG. 2 shows an end view of a trailer system for inspecting the vehicle according to an embodiment of the invention. FIG. 3 shows a schematic view of a wheel set unit 7 in the trailer of the trailer system for inspecting the vehicle according to an embodiment of the invention.

As shown in FIG. 2, the wheel set unit 7 is installed under the trailer frame 1. In an embodiment of the invention, the trailer frame is provided with 4 wheel set units 7 at both sides thereof. However, it will be appreciated for a person skilled in the art to install more than 4 wheel set units 7 in the trailer system as conditions may require. Meanwhile, the auxiliary supporting member 6 is provided at the exit position of the inspection passage, and is located just under a halting position of the trailer at the exit.

Figure 3:
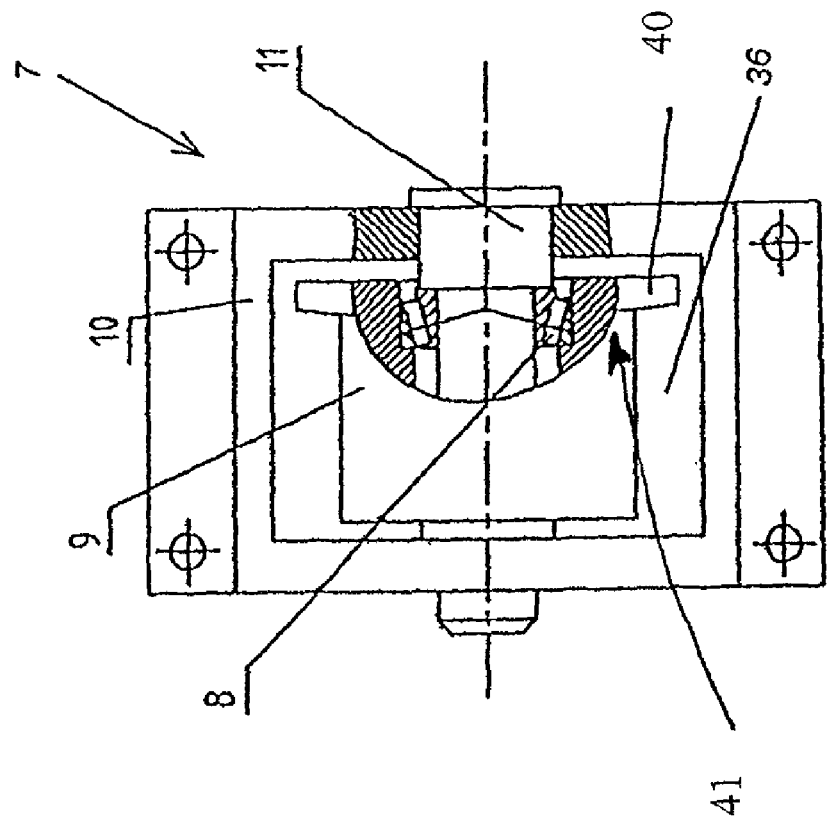
FIG. 3 shows a schematic view of a wheel set unit in the trailer of the trailer system for inspecting the vehicle according to an embodiment of the invention.
Figure 3:
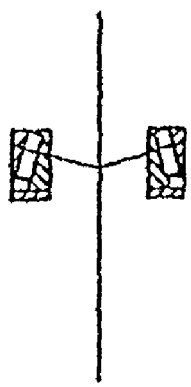

As shown in FIG. 3, the wheel set unit 7 comprises a bearing 8, a wheel 9, a wheel flange 40 located at an inner side 41 of wheel 9, a supporting frame 10, a shaft 11 and an associated structural member 36. The wheel 9 has a center opening for the shaft 11 to be penetrated through, the wheel 9 is engaged with the structural member 36. The shaft 11 is rotatable due to the bearing 8. And the structural member 36 is used for engaging to the trailer frame 1. The supporting frame 10 supports the wheel 9, the shaft 11 and the bearing 8. The shaft 11 is positioned by penetrating through the center opening of the wheel 9. The wheel set unit 7 can be assembled independently, and the wheel set unit 7 is assembled with the trailer frame 1 integrally. A number of the units are uniformly positioned by a mechanically machined face of the trailer frame 1. And such structure with separate units whereas integrally positioned reduces the height of the trailer frame 1 and makes the assembly, disassembly and maintenance easier.

Further from FIG. 2, the auxiliary supporting member 6 does not contact the bottom of the trailer, however, there is a small gap between the auxiliary supporting member 6 and the bottom of the trailer. After the scanning of the vehicle to be inspected (not shown), the trailer dragging (i.e., pulling) the vehicle to be inspected halts just above the auxiliary supporting member 6. When the rear shaft (i.e., axle) of the vehicle to be inspected passes the trailer, since the weight of the rear shaft is normally heavier with larger deflection of the trailer frame, the bottom of the trailer contacts with the auxiliary supporting member 6, which may reduce the deformation of the trailer frame and enhance the bearing capability of the trailer. It should be noted that although two auxiliary supporting members 6 are schematically shown in FIG. 2, there is no specific requirement on the number and shape of the auxiliary supporting member 6, since the auxiliary supporting member 6 only supports the bottom of the trailer, and the shape of the auxiliary supporting member 6 can be rectangular, trapezoid, tape-shaped, plate-shaped, or the like with the number of two or more as required by circumstances. Still further, it is advantageous that the supporting height of the auxiliary supporting member 6 is adjustable.

The turning member 2 of the present invention will be described with reference to FIG. 4, which shows a schematic view of a turning member 2 of a trailer in the trailer system for inspecting the vehicle according to an embodiment of the invention. As indicated above, the turning member 2 shown in FIG. 4 is configured as a turning plate 12.

The turning member 2 comprises a turning plate 12, a chain 13, a guiding rod 14 with an end 14a thereof connected to the chain 13, an adjusting sleeve 15, a spring 16, a bumping shaft 17 and a hinge 18. The turning member 2 is configured to adjust the height and angle of the raised turning plate 12 for abutting against the front wheels 23 of the vehicle to be inspected. The adjusting sleeve 15 is configured to adjust the height and angle of the turning plate 12 abutting against the front wheels 23 of the vehicle to be inspected. It is obvious for those skilled in the art that the adjusting sleeve 15, used as a turning plate brake position adjusting device, can be substituted by other adjusting means for the adjustment of the angle and height of the turning plate 12. For example, the adjusting sleeve 15 can be an angle actuating mechanism provided neighboring the turning plate 12 or a pivot connecting member having a predetermined rotating angle. The above example of the adjusting sleeve 15 is only for illustration purposes rather than for limitation. The adjusting sleeve 15 is fitted over the guiding rod 14, with an end thereof abutting against the spring 16 so that the brake height and angle of the turning plate 12 can be adjusted by the tension degree of the spring 16.

The turning plate 12 can be connected with the trailer body 1 with the hinge 18. However, the connection thereof is not limited to the hinge 18, and the rotatable connection thereof can be implemented in other connecting manner. The chain 13 is connected to the turning plate 12 in a manner such as pin connecting, sliding connection, rolling connection or the like, but is not limited thereto.

When there is no external force F, the spring 16 is compressed, the guiding rod 14 tenses the chain 13 and the turning plate 12 raises. It should be noted that the guiding rod 14 is only an exemplary structure for linking with the turning plate 12. The present invention is not limited thereto. Any connecting member that may implement the falling down of the turning plate 12 when the vehicle to be inspected passes can substitute the guiding rod 14.

When the vehicle to be inspected is loaded, the front wheels of the vehicle to be inspected are driven onto the trailer. the wheels press the turning plates 12 to a horizontal level against the elastic force. After the wheels reach the positioning recess 3 of the trailer frame 1, the turning plate 12 raises under the function of the spring 16. When the trailer reaches the unloading position, the bumping shaft 17 (see FIG. 4) is acted upon by the bumping block 4 on the floor (see FIG. 1) for further compressing the spring 16, the chain 13 relaxes, and the turning plate 12 is substantially in a free state. When the front wheels of the vehicle to be inspected exit the positioning recess 3, the turning plate 12 falls naturally without bumping against the chassis of the vehicle to be inspected and the attachment thereof. When the vehicle to be inspected is driven away, no external force f is applied on the guiding rod 14, and the spring 16 tries to recover the elastic deformation. When the guiding rod 14 strains the chain 13 by a pulling force, the turning plate 12 raises, that is, when the trailer left the exit position moving toward the inlet direction, the turning plate 12 automatically turns under the elastic force of the spring 16.

In an embodiment of the invention, the auxiliary supporting member 6 is provided at the exit side of the inspection passage, i.e., the position where the trailer halts, for better description of the structure, function and effect of the present invention. Preferably, the gap between the upper working surface of the auxiliary supporting member 6 and the lower surface of the trailer frame 1 can be further calculated in a precise manner. After the inspection of the vehicle to be inspected, such as scanning, the trailer drags the vehicle to be inspected so as to halt just above the auxiliary supporting member 6. When the rear shaft of the vehicle to be inspected passes through the trailer, since the rear shaft is relatively heavier, the trailer frame 1 is deflected to an extent that the bottom of the trailer frame 1 contacts the auxiliary supporting member 6, and the weight of the rear shaft is transmitted to the floor by the auxiliary supporting member 6. Thus, the deformation of the trailer frame 1 is reduced and the bearing capability of the trailer is enhanced.

The concrete operation of the invention will be described with reference to the above concrete structure of the trailer system for inspecting the vehicle according to an embodiment of the invention, and the appended figures.

Normally, the trailer is anchored at the loading side, and the turning plate 12 is opened at this time. Then, the vehicle to be inspected runs onto the trailer and is positioned in the positioning recess 3, and the whole system is prepared to be ready. Then the driving system of the trailer starts to work, the turning plate 12 abuts against the front wheels of the vehicle to be inspected preventing the vehicle to be inspected from moving. Under this state, the trailer passes through inspection device or apparatus such as the scanning passage. After the predetermined inspection such as scanning, the trailer runs to unloading position. At this time, the auxiliary supporting member 6 is placed under the trailer, the bumping block 4 on the declining slope 5 abuts against the bumping shaft 17 of the turning member mechanism on the trailer, so that the spring 16 is further compressed, and the tension force of the turning plate 12 is released to be in a free state. At this time, the vehicle to be inspected can be driven away from the inspection device or apparatus. When the rear shaft of the vehicle to be inspected passes the trailer, the auxiliary supporting member 6 can prevent the vehicle from generating larger deflection to ensure the passing of the heavily loaded vehicle whilst the turning plate 12 falls naturally when the front wheels left. When the trailer exits from the exit anchoring position, the turning plate 12 opens again under the function of the spring 16, then the trailer returns to the original loading position for next inspection.

It can be found from the description of the embodiment of the invention that a turning member rotation driving mechanism, such as turning plate rotation driving mechanism 25, (FIG. 4) is implemented by the chain 13, the guiding rod 14, the spring 16, the bumping shaft 17 and the bumping block 4. However, the present invention is not limited thereto since it is only an illustrative embodiment of the invention. In another embodiment, the invention can include a linkage device 29 and an actuating device 28 for implementing the turning member feature. For example, according to one embodiment of the invention, the turning plate rotation driving mechanism 25 comprises a linkage device 29 with an end 30 thereof connected to the turning plate 12; an actuating device 28 with an end thereof attached to the other end 31 of the linkage device 29 to drive the linkage device when the actuating device 28 is applied with external force F so that the turning plate 12 is rotated. For example, the linkage mechanism can be a hydraulic actuating circuit, a gas actuating circuit, or a rotating motor. The actuating device 28 can be the combination of the bumping shaft and the bumping block, or a proximity switch or any other device that can sense a signal indicating that the trailer reaches the unloading position, and the device thereof transmits the signals to the linkage device 29 which further changes the state of the turning plate.

In all, the trailer system for inspecting the vehicle according to the invention can be applied to any system for inspection and measurement especially to radiation imaging inspection system widely used customers, civil airport, and the railway station system. The radiation imaging inspection system comprises an accelerator, a detector, an image acquisition device, a scanning device and an operation and inspection subsystem. Since the components in the radiation imaging inspection system are widely used in the conventional art, the detailed description thereof is omitted for clarity purposes.

In addition, the present invention can also be applied to applications such as cargo transporting and cargo vehicle weighting rather than only being limited to inspection, which therefore also fall under the protection scope of the instant invention.

While the embodiments of the present invention have been described by way of examples taken in conjunction with the accompanying drawings, it should be appreciated that modifications, additions and variations to and from the above described embodiments may be made without deviating from the scope of the present invention which is defined by the accompanying claims

What is claimed is:

1. A trailer system for inspecting a vehicle, comprising:
   a trailer having a trailer body, the trailer bearing the vehicle to be inspected;
   a turning member rotatably provided on an upper surface of the trailer for abutting against wheels of the vehicle to be inspected which has stopped on the trailer; and
   a turning member rotation driving mechanism provided on the trailer for driving the turning member to be rotatable, the turning member rotation driving mechanism including
   a linkage device including a chain with an end thereof connected to the turning member, and
   an actuating device including
   a guiding rod, with an end of the guiding rod being attached to another end of the chain,
   a spring fitting over the guiding rod at a side near a floor auxiliary device, such that before the guiding rod is pressed, the spring exerts a tension elastic force on the guiding rod, and
   a bumping shaft coupled with the guiding rod so that the tension elastic force applied on the guiding rod is counteracted when the bumping shaft is acted upon by a bumping block, which causes the turning member to rotate toward the upper surface of the trailer.

2. The trailer system for inspecting the vehicle according to claim 1, wherein the trailer body has a trailer frame.

3. The trailer system for inspecting the vehicle according to claim 1, wherein the floor auxiliary device is disposed to oppose the trailer in a running direction of the vehicle to be inspected.

4. The trailer system for inspecting the vehicle according to claim 3, wherein the floor auxiliary device includes the bumping block provided at a position on the floor auxiliary device which is opposed to the guiding rod.

5. The trailer system for inspecting the vehicle according to claim 3, wherein the turning member is a turning plate pivotably attached to the trailer body.

6. The trailer system for inspecting the vehicle according to claim 3, wherein the floor auxiliary device includes a declining slope device provided at a side toward a direction where the vehicle being inspected exits the trailer.

7. The trailer system for inspecting the vehicle according to claim 1, wherein the trailer frame includes a positioning recess provided in a running direction of the vehicle to be inspected facing away from the turning member, to be coupled with the turning member for positioning front wheels of the vehicle to be inspected.

8. The trailer system for inspecting the vehicle according to claim 1, wherein a height at both ends of the trailer frame is higher than that at a middle portion thereof to form a concave structure, so that the vehicle to be inspected is not scraped by the middle portion.

9. The trailer system for inspecting the vehicle according to claim 1, wherein the trailer body includes wheel set units provided at both sides of the trailer frame.

* * * * *